(12) United States Patent
Pazenok et al.

(10) Patent No.: US 9,617,220 B2
(45) Date of Patent: Apr. 11, 2017

(54) METHOD FOR THE PREPARATION OF PERFLUOROALKYL CONTAINING PYRAZOLES CARBOXYLATES

(71) Applicant: BAYER CROPSCIENCE AG, Monheim (DE)

(72) Inventors: Sergii Pazenok, Solingen (DE); Winfried Etzel, Leichlingen (DE); Norbert Lui, Odenthal (DE); Arnd Neeff, Burscheid (DE)

(73) Assignee: BAYER CROPSCIENCE AG, Monheim (DE)

( * ) Notice: Subject to any disclaimer, the term of this patent is extended or adjusted under 35 U.S.C. 154(b) by 0 days.

(21) Appl. No.: 14/419,003

(22) PCT Filed: Aug. 2, 2013

(86) PCT No.: PCT/EP2013/066327
§ 371 (c)(1),
(2) Date: Feb. 2, 2015

(87) PCT Pub. No.: WO2014/023667
PCT Pub. Date: Feb. 13, 2014

(65) Prior Publication Data
US 2015/0239846 A1  Aug. 27, 2015

Related U.S. Application Data

(60) Provisional application No. 61/711,958, filed on Oct. 10, 2012.

(30) Foreign Application Priority Data

Aug. 7, 2012 (EP) .................................... 12356016

(51) Int. Cl.
C07D 231/16 (2006.01)
C07C 67/343 (2006.01)
C07C 17/00 (2006.01)

(52) U.S. Cl.
CPC ............ *C07D 231/16* (2013.01); *C07C 17/00* (2013.01); *C07C 67/343* (2013.01)

(58) Field of Classification Search
None
See application file for complete search history.

(56) References Cited

U.S. PATENT DOCUMENTS

| 8,436,191 B2 | 5/2013 | Pazenok et al. |
| 8,772,266 B2 | 7/2014 | Bartels et al. |
| 2013/0079302 A1 | 3/2013 | Benting et al. |
| 2014/0148411 A1 | 5/2014 | Bartels et al. |

FOREIGN PATENT DOCUMENTS

| WO | 2010130767 A2 | 11/2010 |
| WO | 2011061205 A1 | 5/2011 |
| WO | 2011151370 A1 | 12/2011 |

OTHER PUBLICATIONS

International Search Report from corresponding PCT/EP2013/066327, mailed Sep. 24, 2013.
Yuhki et al., "Syntheses of 2-(trifluoromethyl)-1,3-dicarbonyl compounds through direct trifluoromethylation with CFI and their application to fluorinated pyrazoles syntheses", Tetrahedron, Elsevier Science Publishers, Amsterdam, NL, vol. 68, No. 12, Jan. 24, 2012 (Jan. 24, 2012), pp. 2636-2649, XP028461973.
Becker, "Zur Wanderung von Brom in ?-Ketos&xFFFD;ureestern under 1,3-Diketonen under ࿽ber Versuche zur Darstellungeins Cyclopentan-1,3-dions. 1. Mitteilung", Helvetica Chimica Acta, vol. 32, No. 3, Jan. 1, 1949 (Jan. 1, 1949), pp. 1114-1122, XP055026568.
Burton et al., "Fluorinated Organometallics: Perfluoroalkyl and Functionalized Perfluoroalkyl Organometallic Reagents in Organic Synthesis", Tetrah Edron, Elsevi er Sci ence Publishers, Amsterdam, N L, vol. 48, No. 2, Jan. 1, 1992 (Jan. 1, 1992), pp. 189-275, XP002652963.
England, "Fluoroketenes. 10. Synthesis and chemistry of a perfluoroacylketene and a related perfluorovinyl ketone", The Journal of Organic Chemistry, vol. 46, No. I , Jan. 1, 1981 (Jan. 1, 1981), pp. 147-153, XP055045793.

*Primary Examiner* — Kamal Saeed
(74) *Attorney, Agent, or Firm* — McBee Moore Woodward Vanik IP LLC

(57) ABSTRACT

The present invention pertains to a novel process for the preparation of Fluoroalkylpyrazole- or Bisperfluoroalkypyrazole carboxylates comprising a cyclization of Perfluoroalkyl ketoesters with hydrazines.

19 Claims, No Drawings

METHOD FOR THE PREPARATION OF PERFLUOROALKYL CONTAINING PYRAZOLES CARBOXYLATES

CROSS REFERENCE TO RELATED APPLICATIONS

This application is a §371 National Stage Application of PCT/EP2013/066327, filed Aug. 2, 2013, which claims priority to EP 12356016.1, filed Aug. 7, 2012 and U.S. 61/711,958, filed Oct. 10, 2012.

BACKGROUND

Field of the Invention

The present invention pertains to a novel process for the preparation of Fluoroalkylpyrazole- or Bisperfluoroalkypyrazole carboxylates comprising a cyclization of Perfluoroalkyl ketoesters with hydrazines.

Description of Related Art

N-Allyl-3-Perfluoroalkyl-5-Fluoropyrazoles carboxylates are important intermediates for the preparation of agrochemical active ingredients, particularly of fungicides. Correspondingly, N-Alkyl-3-Perfluoroallcyl-5-Fluoropyrazoles carboxylates are described, for example, in the synthesis of fungicidally effective pyrazole carboxamides derivatives (cf e.g. WO 2010/130767), or in the synthesis of fungicidally effective arylalkylpyrazolecarboxamide derivatives and analogues (cf e.g. WO 2011/151370).

Usually, 3-Perfluoroalkyl-5-Fluoro pyrazoles carboxylates are prepared via multistep transformations starting from acetoacetates. The preparative process of 5-fluoro-1-alkyl-3-fluoroalkyl-1H-pyrazole-4-carbonyl chlorides from 5-chloro-1-alkyl-3-fluoroallcyl-1H-pyrazol-4-carbaldehyde is disclosed in WO 2011/061205.

Proceeding from this prior art, the object of the present invention is to provide an improved one step process for the preparation of Fluoroalkylpyrazole- or Bisperfluoroalkypyrazole carboxylates derivatives which can be carried out easily and cost-effectively. The Fluoroalkylpyrazole- or Bisperfluoroalkypyrazole carboxylates obtainable using this desired process should preferably be obtained with high yield and high purity. In particular, the desired process should allow the desired target compounds to be obtained without the need for complex purification methods.

This object is achieved by a novel process for the preparation of Fluoroalkylpyrazole- or Bisperfluoroalkypyrazole carboxylates.

SUMMARY

The present invention thus relates to a new process (A) for the preparation of pyrazole carboxylates of the formula (I)

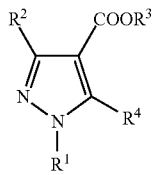
(I)

in which
$R^1$ is hydrogen, $C_1$-$C_6$ Alkyl, Aralkyl or Benzyl,
$R^2$ is $C_1$-$C_5$-Haloalkyl,
$R^3$ is $C_1$-$C_{10}$ alkyl or $C_1$-$C_{10}$-Haloalkyl,
$R^4$ is Cl, F, or $C_1$-$C_5$-Haloalkyl, characterized in that Fluoroalkylacetoactates of formula (II)

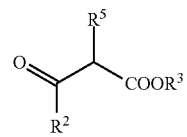
(II)

in which
$R^2$ and $R^3$ are as defined above and
$R^5$ is $C_1$-$C_6$-Haloalkyl,
are reacted with a hydrazine of the formula (III)

$R^1$—NHNH$_2$ (III)

in which $R^1$ is as defined above.

DETAILED DESCRIPTION OF A PREFERRED EMBODIMENT

The process (A) according to the invention can be illustrated by the following formula scheme 1:

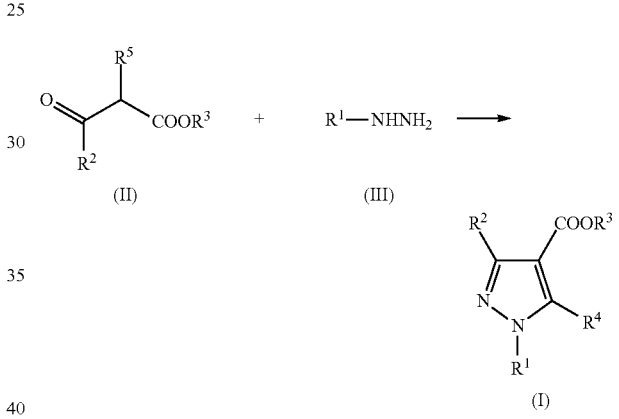

in which $R^1$, $R^2$, $R^3$, $R^4$ and $R^5$ are as defined above.

The radical $R^1$ in these formula (III) and (I) preferably represents a hydrogen atom or $C_1$-$C_5$-Alkyl.

The radical $R^2$ in these formula (II) and (I) preferably represents $HCF_2$, $CF_3$ or $C_2F_5$, and more preferably $HCF_2$.

The radical $R^3$ in these formula (II) and (I) preferably represents $C_1$-$C_5$-Alkyl.

The radical $R^4$ in this formula (I) preferably represents F or $C_1$-$C_5$-Haloalkyl, and more preferably F or $HCF_2$.

The radical $R^5$ in this formula (II) preferably represents $CCl_2F$, $CF_3$, $CF_2Cl$, $CFCl_2$, $CF_2CF_3$, $CF_2CF_2H$, more preferably represents $CCl_2F$, $CF_3$, $CF_2CF_2H$, and even more preferably represents $CF_3$.

Very particular preference is given to the use of the processes according to the invention for the preparation of the following compounds:

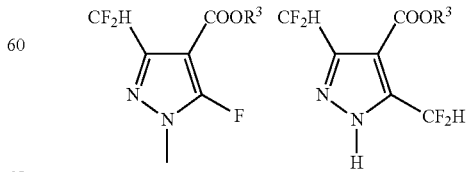

In which $R^3$ is $C_1$-$C_{10}$ Alkyl or $C_1$-$C_{10}$-Haloalkyl, preferably $C_1$-$C_5$-Alkyl.

Some Ketoesters of the formula II ($R^2$=$CF_2H$, $R^5$=$CF_3$) are known (cf. Tetrahedron Letters, 2002 43(43), 7731-7734).

Direct trifluoromethylation of 1,3-dicarbonyl compounds ($R^2$ equals Alkyl) with $CF_3I$ in the presence of a Fenton reagent ($FeSO_4/H_2O_2$) in dimethylsulfoxide is described in Tetrahedron Letters, 2012, 68(12), 2636-2649. 1,3-Diketones, 3-oxocarboxylates, and 3-oxocarboxamides were trifluoromethylated at the methylene carbon between two oxo groups. Cycloaddition of hydrazine derivatives and 2-(trifluoromethyl)-1,3-dicarbonyl compounds provided fluorinated pyrazoles.

Preparation of compounds with $R^2$ equals Haloalkyl is not described in the prior art and their utilization for the preparation of pyrazoles of the formula (I) is unknown.

It was now found that ketoester of the formula (II) can be used for the preparation of the pyrazoles of the formula (I) via reaction with hydrazines.

Two isomers of perfluoroalkylcontaining pyrazoles carboxylates (1a and 1b) could generally be formed when the cyclisation of ketoesters of formula (II) with hydrazines of formula (III) according to scheme 1ab is performed:

Scheme 1 ab

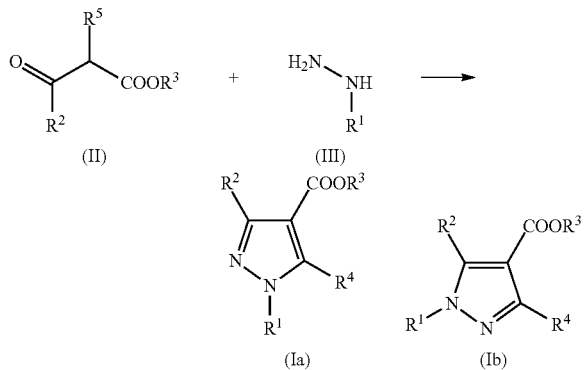

Surprisingly we found that only one isomer pyrazole (Ia) is formed when cyclisation is realized with substituted hydrazine. The reaction proceeds with the participation of the carbonyl function in position 2 and polyfluoralkyl group $R^5$ in position 3. The fluoroalkygroup $R^2$ remains untouched.

According to a further embodiment of the present invention, the cyclisation step with hydrazine is performed in different solvents selected from alcohols, preferably methanol, ethanol, or isopropanol, nitriles, preferably acetonitrile, or butyronitrile, amides, preferably dimethylformamide, or dimethylacetamide, and organic acids, preferably formic acid or acetic acid. Most preferred solvents for the cyclisation are methanol and ethanol, acetic acid.

According to a further embodiment of the present invention, the cyclization is performed at a temperature ranging from 20 to 100° C., more preferably at a temperature ranging from 20° C. to 60° C., most preferably from 20° C. to 50° C.

The reaction time is generally not of critical importance and can depend on the reaction volume; preferably it is within the range of 1 to 5 h.

The ratio of the compound of formula (II) and (III) can vary within a large range; preferably it is within 0.9 and 1.5 equivalents, more preferably between 1 to 1.2 equivalents of hydrazine per one equivalent of the compound of formula (II).

The reaction can be performed in the presence of organic and inorganic bases. Preferred organic bases are: triethylamine, tripropylamine, tributylamin, methydiisopropylamin, N-methylmorpholine, pyridine, alkylpyridines.

Preferred inorganic bases to carry out the reaction are: $NaHCO_3$, $K_2CO_3$, NaOH, $NaHCO_3$.

The amount of base is selected between 1 and 3 equivalents, preferably between 1 and 2 equivalents, more preferably one equivalent of base for one equivalent of compound of formula (II).

The present invention also relates to the use Fluoroalkylacetoactates of formula (II)

in which
$R^2$ is $C_1$-$C_5$-Haloalkyl, preferably $HCF_2$, $CF_3$ or $C_2F_5$ and more preferably $HCF_2$;
$R^3$ is $C_1$-$C_{10}$ Alkyl or $C_1$-$C_{10}$-Haloalkyl, preferably $C_1$-$C_5$Alkyl and
$R^5$ is $C_1$-$C_6$ Haloalkyl, preferably $CCl_2F$, $CF_3$, $CF_2Cl$, $CFCl_2$, $CF_2CF_3$ or $CF_2CF_2H$, more preferably it represents $CCl_2F$, $CF_3$, $CF_2CF_2H$, and even more preferably represents $CF_3$ for the preparation of pyrazole carboxylates of the formula (I)

in which
$R^1$ is hydrogen, $C_1$-$C_6$ Alkyl, Aralkyl or Benzyl; preferably hydrogen or $C_1$-$C_5$ Alkyl;
$R^2$ and $R^3$ are as above defined;
$R^4$ is Cl, F, or $C_1$-$C_5$ Haloalkyl, preferably F or $C_1$-$C_5$-Haloalkyl, and more preferably F or $HCF_2$.

The present invention also provides a new process (B) for the preparation of fluoroalkylacetoactate derivatives of formula (II)

In which $R^2$, $R^3$ and $R^5$ are as defined above, characterized in that haloderivatives of formula (IV)

in which $R^2$ and $R^3$ are as described, above and Hal is halogen,
are reacted with perfluoralkyl copper $CuR^5$ in which $R^5$ is as defined above.

The process (B) according to 2:

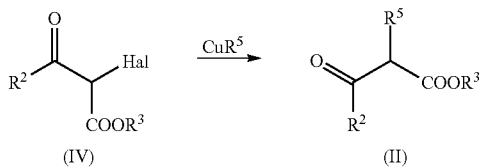

in which $R^2$, $R^3$ and $R^5$ are as herein defined.

Haloderivatives of the formula (IV) are known or obtainable by known methods (Tetrahedron letters, 2009, 65(36), 7538-7552, Izvestiya Akademii Nauk SSSR, Seriya Khimicheskaya, 1984, (5), 1106-14). The preparation of Ethyl 2-Bromo-4,4-difluor-3-oxobutyrcarboxylate is described in WO 2004/014847.

$CuR^5$ can be prepared "in situ" from Perfluoralkyliodide $R^5$—I and Cu (U.S. Pat. No. 3,408,411, Tetrahedron 1969, 25, 5921).

$CF_3Cu$ can be prepared from $CF_3H$ and CuCl (see. Grushin et al, JACS 2011, 133, 20901), $C_2F_5Cu$ from $C_2F_5Si(Me)_3$, CuCl and KF (Kobayashi et al Tetr. Letter 1969, 4095).

The $Hal/R^5$ exchange proceeds in different solvents selected from DMF, DMA or Tetrahydrofurane, Acetonitrile, NMP, Dimethoxyethane or Diglym.

Most preferred solvents for the cyclisation are acetonitrile Acetonitrile, DMF, DMA, NMP.

According to a further embodiment of the present invention, the cyclization is performed at a temperature ranging from 20 to 130° C., more preferably at a temperature ranging from 20° C. to 100° C., most preferably from 20° C. to 80° C.

The reaction time is generally not of critical importance and can depend on the reaction volume, preferably it is within the range of 3 and 15 h.

The ratio of the compound of formula (IV) and $CuR^5$ can vary within a large range, preferably it is within 0.9 and 2.5 equivalents, more preferably between 1 to 2 equivalents, and most preferably 1-1.5 equivalent of $CuR^5$ per one equivalent of the compound of formula (IV).

The present invention also relates to the use of haloderivatives of formula (IV)

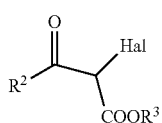

in which
$R^2$ is $C_1$-$C_5$-Haloalkyl, preferably $HCF_2$, $CF_3$ or $C_2F_5$, more preferably $HCF_2$;
$R^3$ is $C_1$-$C_{10}$ Alkyl or $C_1$-$C_{10}$-Haloalkyl, preferably $C_1$-$C_5$-Alkyl,
Hal is Halogen, for preparing fluoroalkylacetoactate derivatives of formula (II)

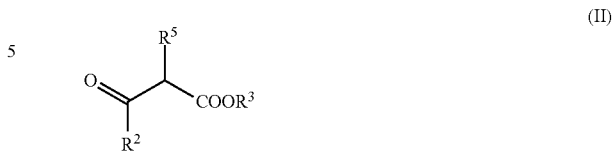

in which
$R^2$ and $R^3$ are as defined above and
$R^5$ is $C_1$-$C_6$-Haloalkyl, preferably $CCl_2F$, $CF_3$, $CF_2Cl$, $CFCl_2$, $CF_2CF_3$ or $CF_2CF_2H$, more preferably $CCl_2F$, $CF_3$, $CF_2CF_2H$, and even more preferably it represents $CF_3$.

The present invention also provides a new process (C) for the preparation of pyrazole carboxylates of the formula (I)

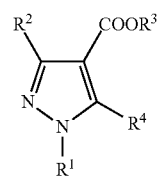

in which $R^1$, $R^2$, $R^3$ and $R^4$ are as defined herein, characterized in that, in a first step, haloderivatives of formula (IV)

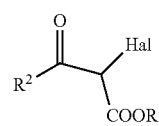

in which $R^2$, $R^3$ and Hal are as above defined,
are reacted with perfluoralkyl copper $CuR^5$ in which $R^5$ is as above described
to obtain fluoroalkylacetoactate derivatives of formula (II)

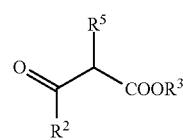

In which $R^2$, $R^3$ and $R^5$ are as above defined,
and the resulting fluoroalkylacetoactate derivatives of formula (II)

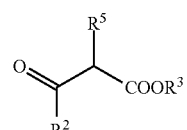

In which $R^2$, $R^3$ and $R^5$ are as above defined,
are reacted with hydrazines of the formula (III)

$R^1$—$NHNH_2$ (III)

In which $R^1$ is as above defined.

The process (C) according to the invention can be illustrated by the following formula scheme 3:

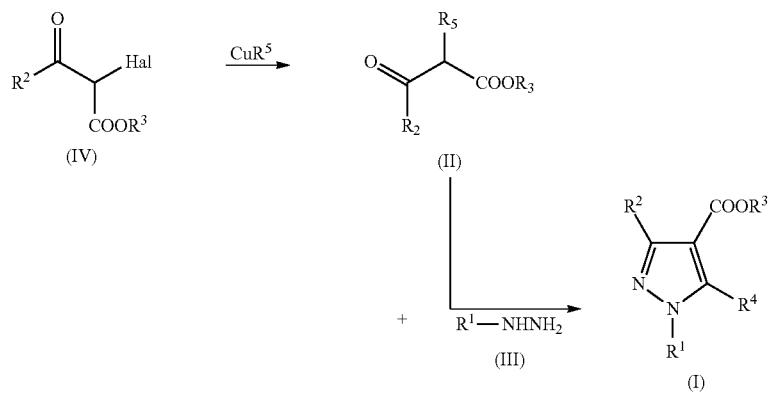

in which $R^1$, $R^2$, $R^3$, $R^4$, $R^5$ and Hal are as herein defined.

The present invention further relates to processes as herein described for the preparation of pyrazole carboxylates of the formula (I) selected among compounds of formula (Ic) or (Id)

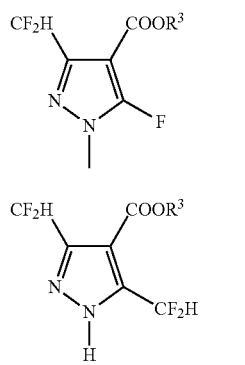

in which $R^3$ is $C_1$-$C_{10}$-Alkyl or $C_1$-$C_{10}$-Haloalkyl, preferably $C_1$-$C_5$-Alkyl.

In connection with the present invention, the term halogen (X or Hal) comprises, unless otherwise defined, those elements which are chosen from the group consisting of fluorine, chlorine, bromine and iodine; fluorine, chlorine and bromine being preferably used and fluorine and chlorine being particularly preferably used.

Appropriately substituted groups can be mono- or polysubstituted, it being possible for the substituents in polysubstitutions to be identical or different.

Alkyl groups substituted with one or more halogen atoms (—X or -Hal) are chosen, for example, from trifluoromethyl ($CF_3$), difluoromethyl ($CHF_2$), $CF_3CH_2$, $C_2F_5$, $ClCH_2$, $CF_2CF_2H$, $CF_3CCl_2$ and $CHF_2CCl_2$.

Allyl groups in connection with the present invention are, unless otherwise defined, linear, branched or cyclic hydrocarbon groups which can optionally exhibit one, two or more heteroatoms chosen from oxygen, nitrogen, phosphorus and sulphur. In addition, the alkyl groups according to the invention can optionally be substituted by additional groups chosen from —R', halogen (X), alkoxy (OR'), thioether or mercapto (SR'), amino (NR'$_2$), silyl (SiR'$_3$), carboxyl (COOR'), cyano (CN), acyl (—(C=O)R') and amide (—CONR'$_2$) groups, R' being hydrogen or a $C_1$-$C_{12}$-alkyl group, preferably a $C_2$-$C_{10}$-alkyl group, particularly preferably a $C_3$-$C_8$-alkyl group, which can exhibit one or more heteroatoms chosen from nitrogen, oxygen, phosphorus and sulphur.

The definition $C_1$-$C_{12}$-alkyl comprises the biggest range defined herein for an alkyl group. Specifically, this definition comprises, for example, the meanings methyl, ethyl, n-propyl, isopropyl, n-butyl, isobutyl, sec-butyl and t-butyl, n-pentyl, n-hexyl, 1,3-dimethylbutyl, 3,3 dimethylbutyl, n-heptyl, n-nonyl, n-decyl, n-undecyl and n-dodecyl.

The definition cyclic $C_3$-$C_{12}$-alkyl groups comprises the biggest range defined herein for a cyclic alkyl group. Specifically, this definition comprises, for example, the meanings cyclopropyl, cyclobutyl, cyclopentyl, cyclohexyl, cycloheptyl and cyclooctyl.

Alkenyl groups in connection with the present invention are, unless otherwise defined, linear, branched or cyclic hydrocarbon groups which comprise at least one single unsaturation (double bond) and can optionally exhibit one, two or more single or double unsaturations or one, two or more heteroatoms chosen from oxygen, nitrogen, phosphorous and sulphur. In addition, the alkenyl groups according to the invention can optionally be substituted by additional groups chosen from —R', halogen (X), alkoxy (OR'), thioether or mercapto (SR'), amino (NR'$_2$), silyl (SiR'$_3$), carboxyl (COOR'), cyano (CN), acyl (—(C=O)R') and amide (—CONR'$_2$) groups, R' being hydrogen or a $C_{1-12}$-alkyl group, preferably a $C_{2-10}$-alkyl group, particularly preferably a $C_{3-8}$-alkyl group, which can exhibit one or more heteroatoms chosen from nitrogen, oxygen, phosphorous and sulphur.

The definition $C_2$-$C_{12}$-alkenyl comprises the biggest range defined herein for an alkenyl group. Specifically, this definition comprises, for example, the meanings vinyl; allyl (2-propenyl), isopropenyl (1-methylethenyl); but-1-enyl (crotyl), but-2-enyl, but-3-enyl; hex-1-enyl, hex-2-enyl, hex-3-enyl, hex-4-enyl, hex-5-enyl; hept-1-enyl, hept-2-enyl, hept-3-enyl, hept-4-enyl, hept-5-enyl, hept-6-enyl; oct-1-enyl, oct-2-enyl, oct-3-enyl, oct-4-enyl, oct-5-enyl, oct-6-enyl, oct-7-enyl; non-1-enyl, non-2-enyl, non-3-enyl, non-4-enyl, non-5-enyl, non-6-enyl, non-7-enyl, non-8-enyl; dec-1-enyl, dec-2-enyl, dec-3-enyl, dec-4-enyl, dec-5-enyl, dec-6-enyl, dec-7-enyl, dec-8-enyl, dec-9-enyl; undec-1-enyl, undec-2-enyl, undec-3-enyl, undec-4-enyl, undec-5- enyl, undec-6-enyl, undec-7-enyl, undec-8-enyl, undec-9-enyl, undec-10-enyl; dodec-1-enyl, dodec-2-enyl, dodec-3-enyl, dodec-4-enyl, dodec-5-enyl, dodec-6-enyl, dodec-7-enyl, dodec-8-enyl, dodec-9-enyl, dodec-10-enyl, dodec-11-enyl; buta 1,3 dienyl, penta-1,3-dienyl.

Alkynyl groups in connection with the present invention are, unless otherwise defined, linear, branched or cyclic hydrocarbon groups which comprise at least one double unsaturation (triple bond) and can optionally exhibit one, two or more single or double unsaturations or one, two or more heteroatoms chosen from oxygen, nitrogen, phosphorous and sulphur. In addition, the alkynyl groups according to the invention can optionally be substituted by additional groups chosen from —R', halogen (X), alkoxy (OR'), thioether or mercapto (SR'), amino (NR'$_2$), silyl (SiR'$_3$), carboxyl (COOR'), cyano (CN), acyl (—(C=O)R') and amide (—CONR'2) groups, R' being hydrogen or a linear, branched or cyclic $C_{1-12}$-alkyl group which can exhibit one or more heteroatoms chosen from nitrogen, oxygen, phosphorous and sulphur.

The definition $C_2$-$C_{12}$-alkynyl comprises the biggest range defined herein for an alkynyl group. Specifically, this definition comprises, for example, the meanings ethynyl (acetylenyl); prop-1-ynyl and prop-2-ynyl.

Aryl groups in connection with the present invention are, unless otherwise defined, aromatic hydrocarbon groups which can exhibit one, two or more heteroatoms chosen from oxygen, nitrogen, phosphorous and sulphur and can optionally be substituted by additional groups chosen from —R', halogen (X), alkoxy (OR'), thioether or mercapto (SR'), amino (NR'$_2$), silyl (SiR'$_3$), carboxyl (COOR'), cyano (CN), acyl (—(C=O)R') and amide (—CONR$_2$') groups, R' being hydrogen or a $C_{1-12}$-alkyl group, preferably a $C_{2-10}$-alkyl group, particularly preferably a $C_{3-8}$-alkyl group, which can exhibit one or more heteroatoms chosen from nitrogen, oxygen, phosphorous and sulphur.

The definition $C_5$-$C_{18}$-aryl comprises the biggest range defined herein for an aryl group having 5 to 18 atoms.

Specifically, this definition comprises, for example, the meanings cyclopenta-idienyl, phenyl, cycloheptatrienyl, cyclooctatetraenyl, naphthyl and anthracenyl.

The definition $C_5$-$C_{18}$-aryl groups exhibiting one, two or more heteroatoms chosen from oxygen, nitrogen, phosphorous and sulphur are chosen, for example, from the group consisting of 2 furyl, 3-furyl, 2-thienyl, 3-thienyl, 2-pyrrolyl, 3-pyrrolyl, 3-isoxazolyl, 4-isoxazolyl, 3-isothiazolyl, 4-isothiazolyl, 5-isothiazolyl, 3-pyrazolyl, 4-pyrazolyl, 5-pyrazolyl, 2 oxazolyl, 4-oxazolyl, 5-oxazolyl, 2-thiazolyl, 4-thiazolyl, 5-thiazolyl, 2-imidazolyl, 4 imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl and 1,3,4-triazol-2-yl; 1 pyrrolyl, 1-pyrazolyl, 1,2,4-triazol-1-yl, 1-imidazolyl, 1,2,3-triazol-1-yl, 1,3,4-triazol-1-yl; 3 pyridazinyl, 4-pyridazinyl, 2-pyrimidinyl, 4-pyrimidinyl, 5-pyrimidinyl, 2-pyrazinyl, 1,3,5 triazin-2-yl and 1,2,4-triazin-3-yl.

Arylalkyl groups (aralkyl groups) in connection with the present invention are, unless otherwise defined, alkyl groups substituted by aryl groups which can exhibit a $C_{1-8}$-alkylene chain and can be substituted in the aryl backbone or the alkylene chain by one or more heteroatoms chosen from oxygen, nitrogen, phosphorous and sulphur and optionally by additional groups chosen from —R', halogen (X), alkoxy (OR'), thioether or mercapto (SR'), amino (NR'$_2$), silyl (SiR'$_3$), carboxyl (COOR'), cyano (CN), acyl (—(C=O)R') and amide (—CONR'$_2$) groups, R' being hydrogen or a $C_{1-12}$-alkyl group, preferably a $C_{2-10}$-alkyl group, particularly preferably a $C_{3-8}$-alkyl group, which can exhibit one or more heteroatoms chosen from nitrogen, oxygen, phosphorous and sulphur.

The definition $C_7$-$C_{19}$-aralkyl group comprises the biggest range defined herein for an arylalkyl group with a total of 7 to 19 atoms in the backbone and alkylene chain. Preference is given to those $C_7$-$C_{19}$-aralkyl groups comprising 5 or 6 carbon atoms or heteroatoms in the aryl backbone and 1 to 8 carbon atoms in the alkylene chain. Specifically, this definition comprises, for example, the meanings benzyl and phenylethyl.

Alkylaryl groups (alkaryl groups) in connection with the present invention are, unless otherwise defined, aryl groups substituted by alkyl groups which can exhibit a $C_1$-$C_8$-alkylene chain and can be substituted in the aryl backbone or the alkylene chain by one or more heteroatoms chosen from oxygen, nitrogen, phosphorous and sulphur and optionally by additional groups chosen from —R', halogen (X), alkoxy (OR'), thioether or mercapto (SR'), amino (NR'$_2$), silyl (SiR'$_3$), carboxyl (COOR'), cyano (CN), acyl (—(C=O)R') and amide (CONR'$_2$) groups, R' being hydrogen or a $C_1$-$C_{12}$-alkyl group, preferably a $C_2$-$C_{10}$-alkyl group, particularly preferably a $C_3$-$C_8$-alkyl group, which can exhibit one or more heteroatoms chosen from nitrogen, oxygen, phosphorous and sulphur.

The definition $C_7$-$C_{19}$-alkylaryl group comprises the biggest range defined herein for an alkylaryl group with a total of 7 to 19 atoms in the backbone and alkylene chain. Preference is given to those $C_7$-$C_{19}$-aralkyl groups comprising 5 or 6 carbon atoms or heteroatoms in the aryl backbone and 1 to 8 carbon atoms in the alkylene chain. Specifically, this definition comprises, for example, the meanings tolyl-, 2,3-, 2,4-, 2,5-, 2,6-, 3,4- or 3,5-dimethylphenyl.

The alkyl, alkenyl, alkynyl, aryl, alkylaryl and aralkyl groups can furthermore exhibit one or more heteroatoms which, unless otherwise defined, are chosen from nitrogen, oxygen, phosphorous and sulphur. The heteroatoms in this connection replace the carbon atoms indicated.

The compounds according to the invention can exist, if appropriate, as mixtures of different possible isomeric forms, in particular of stereoisomers, such as, e.g., E and Z isomers, threo and erythro isomers, and optical isomers, but, if appropriate, also tautomers. Both the E and Z isomers, as also the threo and erythro isomers, and also the optical isomers, any mixture of these isomers, and the possible tautomeric forms, are disclosed and claimed.

EXAMPLES

Example 1

4,4-difluoro-3-oxo-2-(trifluoromethyl)butatioate

Ethyl 4,4-difluoro-3-oxo-2-butanoate 40 g (241 nunol) was dissolved in 600 ml DMSO and water solution of $FeSO_4$ (723 mmol) was added while the temperature was kept below 40° C. 98 g of $CF_3I$ was added in a slow stream of gas while at the same time $H_2O_2$ (35% solution in water, 482 mmol) as added slowly within 15 min. The mixture was cooled du icing the addition. The mixture was stirred at room temperature for 30 min. The conversion of the Ethyl 4,4-ditluoro-3-oxo-2-butanoate was found to be 86%. The mixture was poured carefully into 1.5 L of water under cooling. The product was exptracted with Methylter.tbutylether, washed with with water and brine and dried over $Na_2SO_4$.

The solvent was removed to give 48 g of the product (as a mixture with hydrate) with purity of 90% as a mixture of two compounds.

$^1$H NMR (CDCl3) (t, 3H); 4.4 (q, CH2); 4.7 (q, 1H, 9 Hz), 5.9 (t, 1H, 48 Hz) ppm.

$^{19}$F NMR (CDCl3); 63.5 (d, 3F). 126.9 (3't, 3F) ppm.

$^{13}$C NMR (CDCl3):

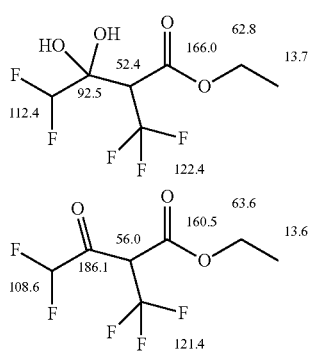

Example 2

4,4-difluoro-3-oxo-2-(trifluoromethyl)butatioate 24.5 g of ethyl 2-bromo-4,4-difluoro-3-oxobutanoate (prepared according and CuCF$_3$ prepared from (CF$_3$H according to the procedure described in JACS. 2011, 133, 20901-20913) were mixed together in 40 ml CH$_3$CN and the mixture stirred for 10 h at 40° C. GC showed the full conversion and the formation of the desired product. The mixture was cooled and poured on 500 ml of ice water The product was extracted with Methylter.tbutylether, washed with with water and brine and dried over Na$_2$SO$_4$.

The solvent was removed to give 20 g of the product with purity of 90%. The product was used without purification for the next step.

Example 3

Ethyl 1-Methyl-3-clifluoromethyl-5-fluoro-1H-pyrazolcarboxylate 2.34 g (0.01 mol) of ethyl 4,4-difluoro-3-oxo-2-(trifluoromethyl)butanoate, and 0.46 g methylhydrazin were mixed together in 10 ml acetonitrile. Reaction mixture was kept 5 h at 30° C. The solvent was removed in vacuuo and the product was isolated via column chroniatografie on SiO$_2$ using Ethylacetate hexane. Yield 58%.

Mass spectra (ESPI) positive m/z 223.

$^1$H NMR: 1.2/t, 3H); 3.6 (s, 3H), 4.16 (q, 2H); 6.92 (t, 1H)

$^1$H NMR: 1.2/t, 3H); 3.6 (s, 3H); 4.16 (q, 2H); 6.92 (t, 1H).

$^{13}$C NMR (CD3CN):

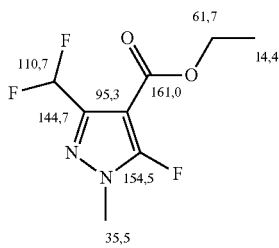

Example 4

Ethyl 1-phenyl1-3-difluoromethyl-5-fluoro-1H-pyrazolcarboxylate

Similar prepared from 4,4-difluoro-3-oxo-2-(trifluoromethypbutarioate and phenylhydrazine.
Yield 63%.
$^{13}$C NMR (CDCl3).

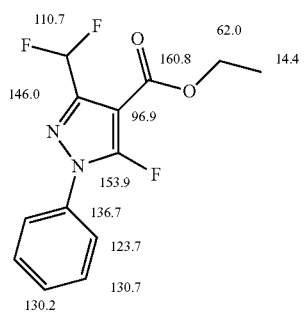

The invention claimed is:
1. Process for preparing a pyrazole carboxylate of formula (I)

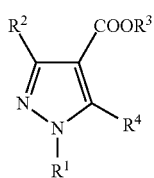

in which
R$^1$ is hydrogen, C$_1$-C$_6$-Alkyl, Aralkyl or Benzyl;
R$^2$ is C$_1$-C$_5$-Haloalkyl,
R$^3$ is C$_1$-C$_{10}$-Alkyl or C$_1$-C$_{10}$-Haloalkyl,
R$^4$ is Cl, F, or C$_1$-C$_5$ Haloalkyl,
wherein, a haloderivative of formula (IV)

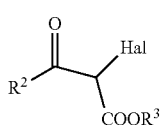

in which R$^2$ and R$^3$ are as above defined, and Hal is halogen, is reacted with perfluoroalkyl copper $CuR^5$ in which $R^5$ is $C_1$-$C_6$ Haloalkyl,
to obtain a fluoroalkylacetoactate derivative of formula (II)

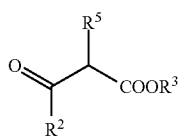
(II)

in which $R^2$, $R^3$ and $R^5$ are as above defined, and the resulting fluoroalkylacetoactate derivative of formula (II)

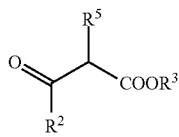
(II)

in which $R^2$, $R^3$ and $R^5$ are as above defined,
is reacted with a hydrazine of formula (III)

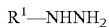
$R^1$—$NHNH_2$ (III)

in which $R^1$ is as above defined.

2. Process according to claim 1 wherein the pyrazole carboxylate of formula (I) is selected among compounds of formula (Ic) or (Id)

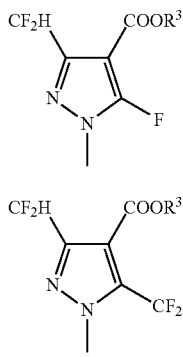
(Ic)

(Id)

in which $R^3$ is $C_1$-$C_{10}$-Alkyl or $C_1$-$C_{10}$-Haloalkyl.

3. The process according to claim 1, wherein $R^1$ is hydrogen.

4. The process according to claim 1, wherein $R^2$ is $HCF_2$, $CF_3$ or $C_2F_5$.

5. The process according to claim 1, wherein $R^3$ is $C_1$-$C_5$-alkyl.

6. The process according to claim 1, wherein $R^4$ is Cl or F.

7. The process according to claim 1, wherein $R^4$ is $C_1$-$C_5$-haloalkyl.

8. The process according to claim 1, wherein $R^1$ is $C_1$-$C_6$-alkyl.

9. The process according to claim 1, wherein $R^1$ is aralkyl.

10. The process according to claim 1, wherein $R^1$ is benzyl.

11. The process according to claim 1, wherein $R^3$ is $C_1$-$C_{10}$-alkyl.

12. The process according to claim 1, wherein $R^3$ is $C_1$-$C_{10}$-haloalkyl.

13. The process according to claim 1, wherein the haloderivative of formula (IV) is ethyl 2-bromo-4,4-difluoro-3-oxobutanoate.

14. The process according to claim 1, wherein $R^5$ is $CCl_2F$, $CF_3$, $CF_2Cl$, $CFCl_2$, $CF_2CF_3$ or $CF_2CF_2H$.

15. The process according to claim 8, wherein $R^2$ is $HCF_2$, $R^3$ is $C_1$-$C_5$-Alkyl and $R^5$ is $CF_3$.

16. Process for preparing a fluoroalkylacetoactate derivative of formula (II)

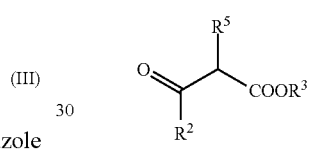
(II)

in which
$R^2$ is $C_1$-$C_5$-Haloalkyl,
$R^3$ is $C_1$-$C_{10}$-Alkyl or $C_1$-$C_{10}$-Haloalkyl,
$R^5$ is $C_1$-$C_6$-Haloalkyl,
comprising reacting a haloderivative of formula (IV)

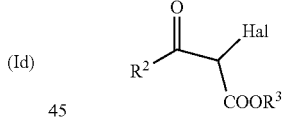
(IV)

in which
$R^2$, $R^3$ are as above described, and Hal is halogen;
with perfluoroalkyl copper $CuR^5$ in which $R^5$ is as above described.

17. Process according to claim 16 wherein $R^2$ is $HCF_2$, $R^3$ is $C_1$-$C_5$-Alkyl and $R^5$ is $CF_3$.

18. The process according to claim 16 wherein $R^2$ is $HCF_2$, $R^3$ is $C_1$-$C_5$-Alkyl and $R^5$ is $CF_3$.

19. A process of preparing a fungicide prepared by a process comprising the process of claim 1.

* * * * *